(12) United States Patent
Jang et al.

(10) Patent No.: US 12,742,758 B2
(45) Date of Patent: Sep. 22, 2026

(54) SENSOR DEVICE FOR A MOBILE ROBOT

(71) Applicants: HYUNDAI MOTOR COMPANY, Seoul (KR); KIA CORPORATION, Seoul (KR)

(72) Inventors: Sungtai Jang, Ulsan (KR); Changmo Yang, Hwaseong-si (KR)

(73) Assignees: HYUNDAI MOTOR COMPANY, Seoul (KR); KIA CORPORATION, Seoul (KR)

( * ) Notice: Subject to any disclaimer, the term of this patent is extended or adjusted under 35 U.S.C. 154(b) by 394 days.

(21) Appl. No.: 18/489,312

(22) Filed: Oct. 18, 2023

(65) Prior Publication Data

US 2025/0027923 A1 Jan. 23, 2025

(30) Foreign Application Priority Data

Jul. 18, 2023 (KR) ........................ 10-2023-0092821

(51) Int. Cl.
*G01N 33/00* (2006.01)

(52) U.S. Cl.
CPC ................................ *G01N 33/0027* (2013.01)

(58) Field of Classification Search
CPC . B25J 19/02; B25J 19/0054; G01N 2001/245; G01N 2001/2282; G01N 25/145; G01N 25/4826; G01N 2035/00346; G01N 2035/00445; G01N 2203/0228; B01L 7/00; B01L 2300/1844; F21V 29/67; F21V 29/673; F21V 29/677; F21V 29/00; F21V 29/50; H05K 7/20136; H05K 7/202; H05K 7/20209; H05K 7/20754; H05K 7/20172; H05K 7/2019
USPC ....... 73/31.2, 23.4, 23.42, 24.6, 25.5, 335.2, 73/29.5, 30.4, 31.5, 54.16, 61.56, 61.58, 73/61.61, 61.68, 204.23, 863.11
See application file for complete search history.

(56) References Cited

U.S. PATENT DOCUMENTS

2019/0033897 A1* 1/2019 Barbier .................... G06F 1/206
2023/0398483 A1* 12/2023 Mecham ................ G08B 21/12

FOREIGN PATENT DOCUMENTS

KR 102073028 B1 2/2020
KR 102237432 B1 4/2021
KR 102333316 B1 12/2021

* cited by examiner

*Primary Examiner* — John E Breene
*Assistant Examiner* — Truong D Phan
(74) *Attorney, Agent, or Firm* — Lempia Summerfield Katz LLC

(57) ABSTRACT

A sensor device may include: a sensor housing forming a mounting space and having a first vent and a second vent through which air flows in and out; a plurality of sensor modules provided in the mounting space of the sensor housing; a first door and a second door configured to selectively block the first and second vents of the sensor housing, respectively; an opening/closing device configured to operate the first and the second doors; and a first fan and a second fan configured to introduce air into the sensor housing, or discharge air inside the sensor housing to an outside.

14 Claims, 14 Drawing Sheets

SENSOR DEVICE FOR A MOBILE ROBOT

CROSS-REFERENCE TO RELATED APPLICATION

This application claims priority to and the benefit of Korean Patent Application No. 10-2023-0092821, filed on Jul. 18, 2023, the entire contents of which are incorporated herein by reference.

BACKGROUND

(a) Technical Field

The present disclosure relates to a sensor device for a mobile robot.

(b) Description of the Related Art

In industrial sites such as vehicle manufacturing plants, various harmful gases (e.g., dioxide gas, methane gas, and the like) harmful to the human body are used. If such harmful gas leaks due to an abnormal cause, fatal harm may be applied to workers working in industrial sites.

In order to solve this problem, research is being conducted on a technology for checking the safety of an industrial site using a mobile robot such as a walking robot or a wheel-driven robot. To this end, the use of various sensors installed on a mobile robot, which detect pollutants (or harmful gases, and the like) through the sensors, is employed to inspect the safety of industrial sites.

However, when a load on the mobile robot is increased by various sensors, the power consumption of the battery is increased. As a result, a problem may arise in that the operating time (or mileage) of the mobile robot is reduced.

The above information disclosed in this Background section is provided only to enhance understanding of the background of the disclosure. Therefore, the background section may contain information that does not form the prior art that is already known to a person of ordinary skill in the art.

SUMMARY

Embodiments of the present disclosure provide a sensor device for a mobile robot capable of increasing the operating time or travel distance of a mobile robot by decreasing the load of a sensor device.

In one embodiment, the sensor device may include a sensor housing forming a mounting space and having a first vent and a second vent through which air flows in and out. The sensor device may also include a plurality of sensor modules provided in the mounting space of the sensor housing, and a first door and a second door configured to selectively block the first and second vents of the sensor housing, respectively. The sensor device may also include an opening/closing device configured to operate the first and the second doors. Furthermore, the sensor device may include a first fan and a second fan configured to introduce air into the sensor housing, or discharge air inside the sensor housing to an outside.

In one embodiment, a sensor module of the plurality of sensor modules may include a sensing unit configured to detect a chemical substance contained in the air introduced into the sensor housing. The sensor module may also include an interface unit configured to directly transmit the signal detected by the sensing unit to a mobile unit.

In another embodiment, the opening/closing device may include a driving unit configured to generate power, and a power delivery device configured to transfer the power generated by the driving unit to the first and second doors.

In one embodiment, the power delivery device may include a worm wheel provided on a drive shaft of the driving unit, and a worm gear provided on a transfer shaft and engaged with the worm wheel. The power delivery device may further include a pair of intermediate gears. Each intermediate gear may be provided on a side of the transfer shaft. The power delivery device may further include a rack gear provided on each of the first and the second doors, and engaged with each intermediate gear.

In one embodiment, the first and second vents may be provided on both side surfaces of the sensor housing, respectively. The first and the second doors may be provided on the first and second vents, respectively. The first and the second fan may be provided on the first and second vents, respectively.

The first and second vents may be disposed to face each other.

In one embodiment, a sensor device may further include an air induction device configured to guide air from the first and second vents to pass through the plurality of sensor modules.

The air induction device may include a bottom plate, and an upper plate configured to form a seating portion on which a sensor module of the plurality of sensor modules is seated in cooperation with the bottom plate. The air induction device may further include at least one partition wall provided between the bottom plate and the upper plate and configured to form the seating portion on which the sensor module of the plurality of sensor modules is seated in cooperation with the bottom plate and the upper plate. Additionally, an air induction hole is formed on the at least one partition wall.

At a sensing position for measuring pollutants of external air, the first door and the second door may be opened. The first fan may operate in a direction to introduce air into the mounting space, and the second fan may operate in a direction to discharge air from the mounting space to the outside.

At a calibration position to calibrate a sensor module of the plurality of sensor modules, the first door and the second door may be opened. Additionally, the first fan and the second fan may operate in a direction to discharge air from the mounting space to the outside so as to form negative pressure in the mounting space.

In one embodiment, a sensor device may include a sensor housing forming a mounting space and having a first vent and a second vent through which air flows in and out. The sensor device may also include a plurality of sensor modules provided in the mounting space of the sensor housing, a first fan provided on the first vent, and a second fan provided on the second vent.

The first and second vents may be provided to face each other.

In one embodiment, the sensor device may further include an air induction device configured to guide air from the first and second vents to pass through the plurality of sensor modules.

The air induction device may include a bottom plate, and an upper plate configured to form a seating portion on which a sensor module of the plurality of sensor modules is seated in cooperation with the bottom plate. The air induction device may further include at least one partition wall provided between the bottom plate and the upper plate, and the at least one partition wall is configured to form the seating portion on which the sensor module of the plurality of sensor modules is seated in cooperation with the bottom plate and the upper plate. Additionally, an air induction hole is formed in the at least one partition wall.

At a sensing position to measure pollutants of external air, the first fan may operate in a direction to introduce air into the mounting space, and the second fan may operate in a direction to discharge air from the mounting space.

At a calibration position to calibrate a sensor module of the plurality of sensor modules, the first fan and the second fan may operate in a direction to discharge air from the mounting space to an outside so as to form negative pressure in the mounting space.

According to a sensor device for a mobile robot according to the present disclosure, the operating time or travel distance of the mobile robot may be increased by reducing the weight of the sensor device mounted on the mobile robot.

In addition, reliability of the sensor module may be improved through a calibration operation of the sensor module mounted on the mobile robot.

Other effects that may be obtained or are predicted by an embodiment are explicitly or implicitly described in a detailed description of the present disclosure. In other words, various effects that are predicted according to an embodiment are described in the following detailed description.

BRIEF DESCRIPTION OF THE DRAWINGS

These drawings are for reference only in describing embodiments of the present disclosure. Therefore, the technical idea of the present disclosure should not be limited to the accompanying drawings.

Figure 1:
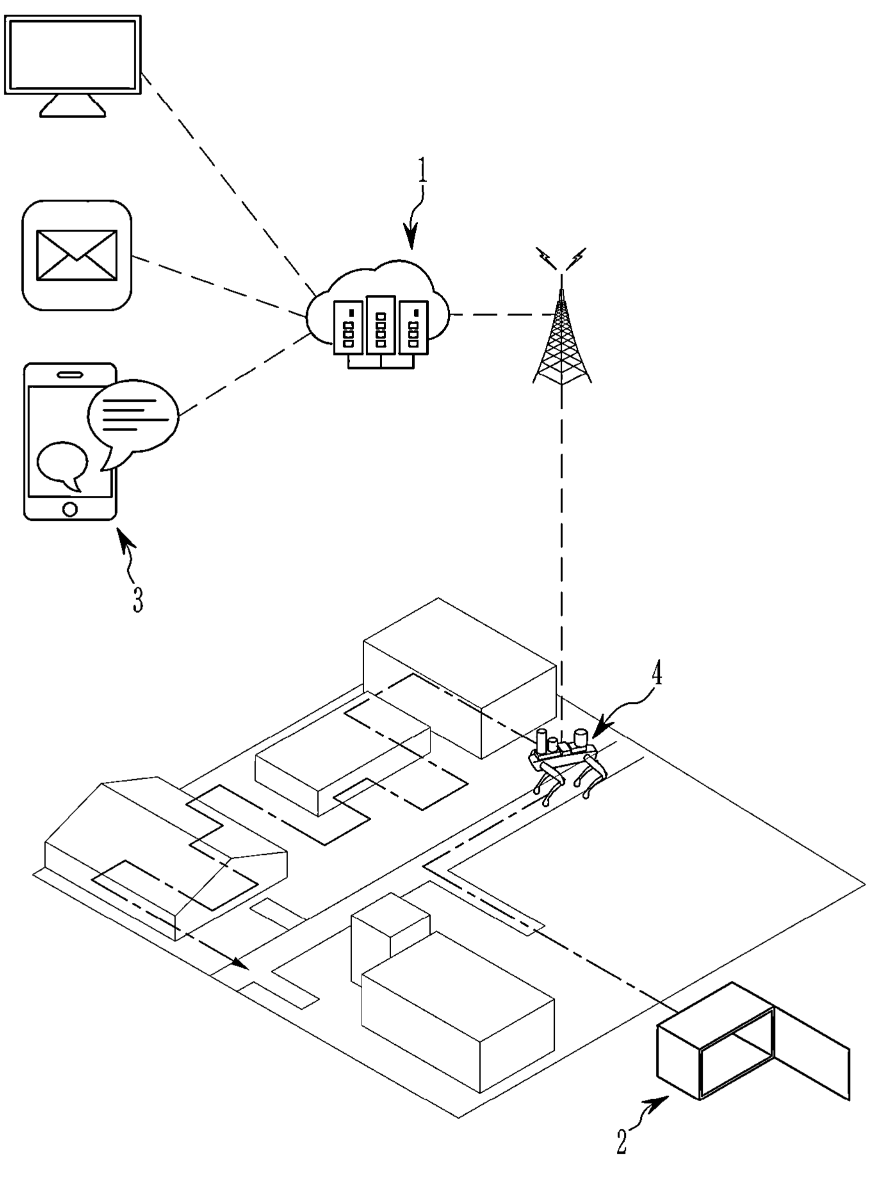
FIG. 1 is a schematic view showing a configuration of a control system according to an embodiment of the present disclosure.

It should be understood that the above-referenced drawings are not necessarily drawn to scale, thus present a somewhat simplified representation of various features illustrative of the basic principles of the disclosure. The specific design features of the present disclosure, including, for example, specific dimensions, orientations, locations, and shapes, will be determined in part by the particular intended application and use environment.

DETAILED DESCRIPTION

The terminology used herein is for the purpose of describing particular embodiments only and is not intended to be limiting of the present disclosure. As used herein, the singular forms are intended to include the plural forms as well, unless the context clearly indicates otherwise. As used herein, the term "comprises" and/or "comprising" refers to the presence of specified features, integers, steps, acts, elements and/or components, but it should also be understood that it does not exclude a presence or an addition of one or more other features, integers, steps, acts, components, and/or groups thereof. As used herein, the term "and/or" includes any one or all combinations of one or more related items.

When a component, device, element, or the like of the present disclosure is described as having a purpose or performing an operation, function, or the like, the component, device, or element should be considered herein as being "configured to" meet that purpose or perform that operation or function.

The present disclosure will be described more fully hereinafter with reference to the accompanying drawings, in which embodiments of the disclosure are shown. Those having ordinary skill in the art should realize that the described embodiments may be modified in various different ways, all without departing from the spirit or scope of the present disclosure.

The drawings and description are to be regarded as illustrative in nature and not restrictive, and like reference numerals designate like elements throughout the specification.

In addition, the size and thickness of each configuration shown in the drawings are arbitrarily shown for understanding and ease of description, but the present disclosure is not limited thereto. Additionally, to clearly illustrate several portions and regions, the thicknesses of each configuration thereof are increased.

The term "unit" or "module" used in this specification signifies one unit that processes at least one function or operation, and may be realized by hardware, software, or a combination thereof. The operations of the method or the functions described in connection with the forms disclosed herein may be embodied directly in a hardware or a software module executed by a processor, or in a combination thereof.

In describing embodiments of the present specification, when it is determined that a detailed description of the well-known art associated with the present disclosure may obscure the gist of the present disclosure, it is omitted.

The accompanying drawings are provided only in order to allow embodiments disclosed in the present specification to be easily understood and are not to be interpreted as limiting the spirit disclosed in the present specification. Additionally, it is to be understood that the present disclosure includes all modifications, equivalents, and substitutions without departing from the scope and spirit of the present disclosure.

Terms including ordinal numbers such as first and second may be used to describe various components, but are not to be interpreted as limiting these components.

First, a control system including a mobile robot equipped with a sensor device is described.

Figure 2:
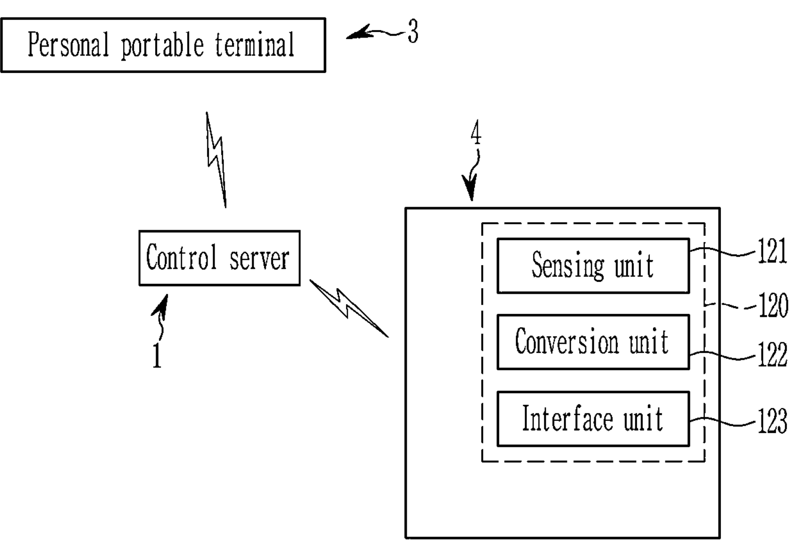
FIG. 2 is a block diagram showing a configuration of a control system according to an embodiment of the present disclosure.

FIG. 1 is a schematic view showing a configuration of a control system according to the present disclosure. FIG. 2 is a block diagram showing a configuration of a control system according to the present disclosure. In addition, FIG. 3 is a perspective view showing a configuration of a mobile robot according to the present disclosure.

Figure 3:
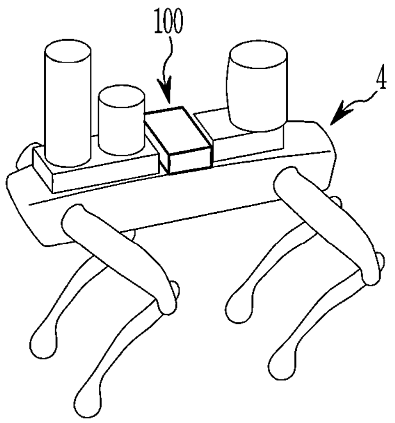
FIG. 3 is a perspective view illustrating a configuration of a mobile robot according to an embodiment of the present disclosure.

As shown in FIGS. 1-3, a control system according to the present disclosure may include a mobile robot 4 equipped with a sensor device 100, and a control server 1 connected to the mobile robot 4 through a wireless network. The control system may also include a personal portable terminal 3 connected to the control server 1 through a wireless network.

The mobile robot 4 may be connected to the control server 1 through the wireless network to transmit and receive data. The control server 1 may be connected to a portable terminal of a manager through the wireless network to transmit and receive data.

In the present disclosure, the mobile robot 4 equipped with the sensor device 100 is described to be a 4-legged mobile robot as a mere example. However, the scope of the present disclosure is not limited thereto, and may also be applied to a wheel-based mobile robot.

The mobile robot 4 equipped with the sensor device 100 according to the present disclosure is configured to measure pollutants at a predetermined position while moving inside and outside of an industry site (e.g., manufacturing factory) according to instructions of the control server 1.

When the mobile robot 4 is positioned at the predetermined position (e.g., a sensing position), the sensor device 100 measures pollutants (e.g., carbon dioxide, methane gas, or the like) included in the external air, and may transmit the measured results to the control server 1. Information including the type of pollutant and/or the concentration of the pollutant measured by the sensor device 100 may be transmitted to the control server 1.

When it is determined from the sensor device 100 of the mobile robot 4 that the pollutant has leaked at the predetermined position, the control server 1 may transmit a message (e.g., text message) to the personal portable terminal 3 of the manager. Through this, the manager may take immediate action on the site where the pollutant is leaked.

If necessary, when the mobile robot 4 is positioned at the predetermined position (e.g., calibration position) outside an industry site, the sensor device 100 may perform a calibration operation. The calibration operation may refer to a process of desorbing pollutants adsorbed on the sensor device 100 by allowing fresh air from the outside to flow into the sensor device 100.

Hereinafter, the sensor device 100 according to the present disclosure is described in detail with reference to the accompanying drawings.

Figure 4:
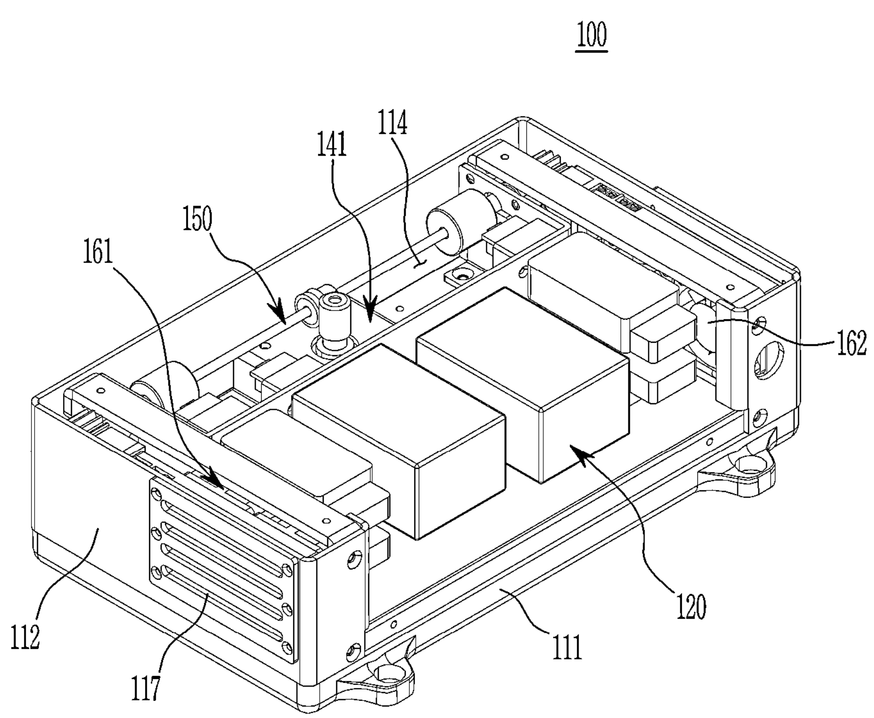
FIG. 4 is a perspective view illustrating a configuration of a sensor device according to an embodiment of the present disclosure.

FIG. 4 is a perspective view showing a configuration of a sensor device 100 according to the present disclosure. In addition, FIGS. 5 and 6 are exploded perspective views showing a configuration of a sensor device 100 according to the present disclosure.

Figure 5:
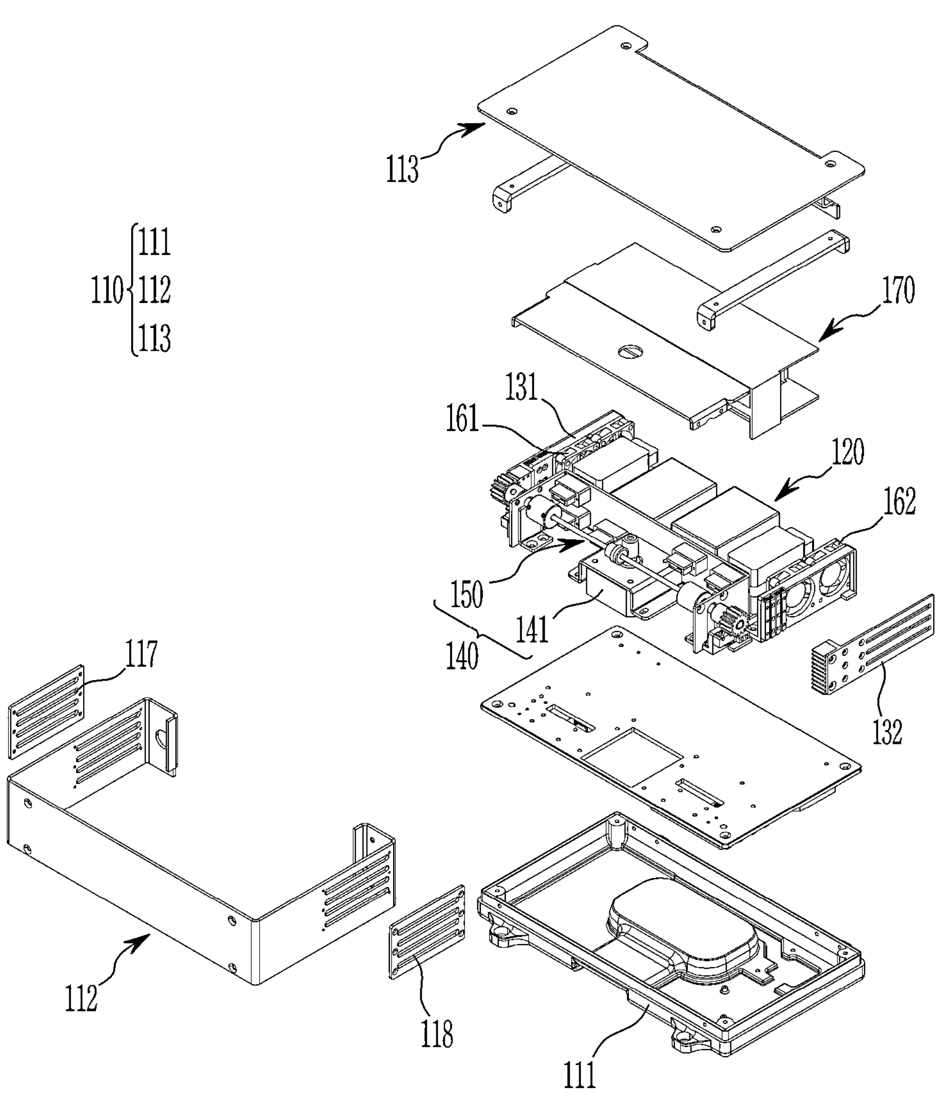
FIGS. 5 and 6 are exploded perspective views illustrating a configuration of a sensor device according to embodiments of the present disclosure.
Figure 6:
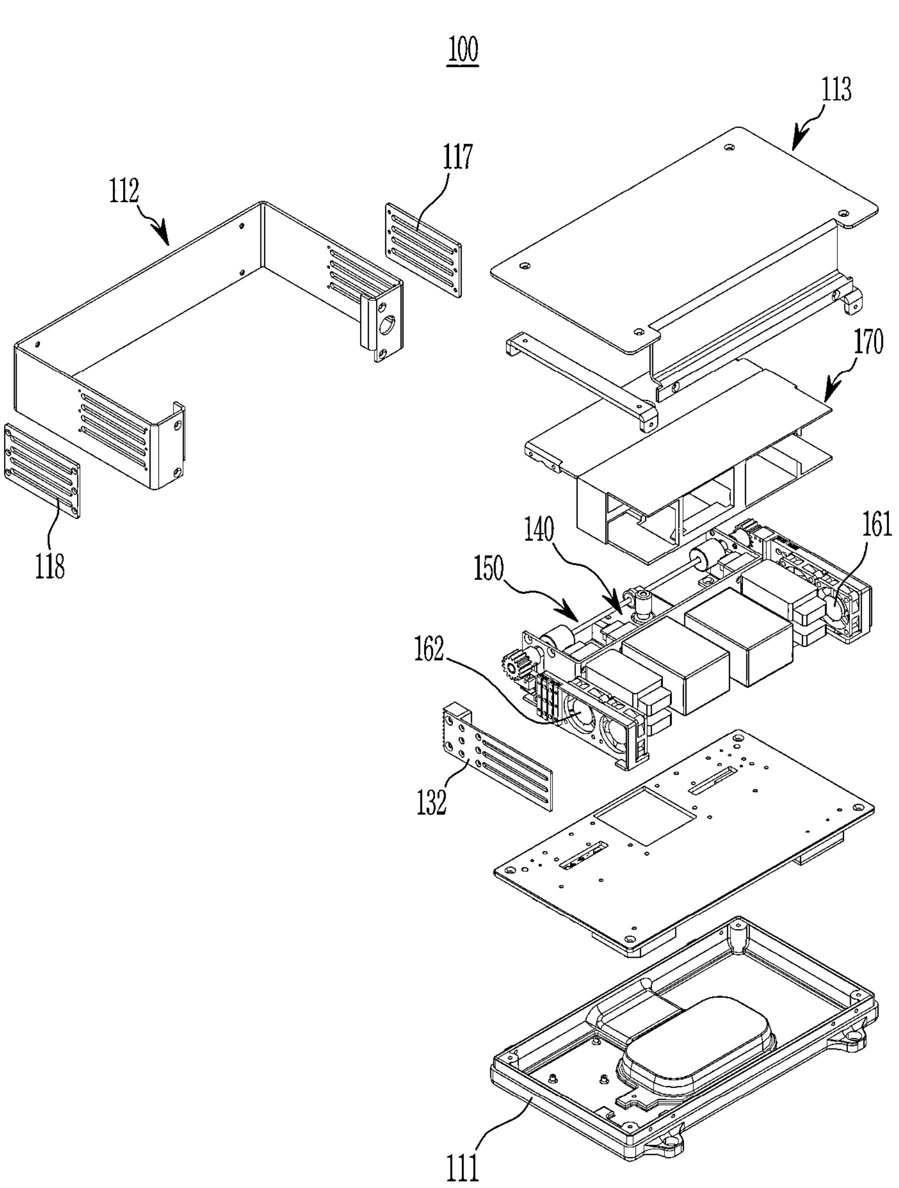

Referring to FIGS. 4-6, the sensor device 100 according to the present disclosure may include a sensor housing 110 forming a mounting space 114 and a pair of vents. The sensor device 100 may also include at least one sensor module 120 provided inside the sensor housing 110, and a pair of doors (131, 132) configured to selectively block the pair of vents (117, 118) of the sensor housing 110. The sensor device 100 may also include an opening/closing device 140 configured to operate the pair of doors (131, 132), and a pair of fans (161, 162) configured to introduce air into the sensor housing 110 or discharge air inside the sensor housing 110 to an outside.

The sensor housing 110 may include a lower case 111, an intermediate case 112, and an upper case 113. The lower case 111 is formed in a generally plate shape. The intermediate case 112 is positioned on an upper portion of the lower case 111 and formed in a generally '⊔' shape. The intermediate case 112 has a first side surface formed with a first vent 117 and a second side surface formed with a second vent 118. The first vent 117 and the second vent 118 may be disposed to face each other. The upper case 113 is positioned on an upper portion of the intermediate case 112, and formed in a generally plate shape. The lower case 111, the intermediate case 112, and the upper case 113 may cooperatively form the mounting space 114 on which various component parts are mounted in.

At least one sensor module 120 may be disposed in the mounting space 114 of the sensor housing 110. In the present disclosure, a plurality of sensor modules 120 are provided, and for example, four sensor modules 120 may be disposed in the mounting space 114 of the sensor housing 110.

The sensor module 120 may include a sensing unit 121 configured to detect pollutants (or, a chemical substance) contained in the air introduced into the sensor housing 110, and an interface unit 123 configured to transmit the signal detected by the sensing unit 121. In the present disclosure, the sensor module 120 may be a chemical sensor that detects chemical substances contained in the air. For example, the sensor module 120 may be a gas sensor that detects carbon dioxide (CO2), methane (CH4), and the like. In the present disclosure, the sensor module 120 is not provided with a separate signal processor and/or a battery, and is only provided with the sensing unit 121 and the interface unit 123 configured to transmit the signal detected by the sensing unit 121 to the mobile robot 4. In the present disclosure, since the signal detected by the sensing unit 121 is transmitted to the processor of the mobile robot 4, the sensor module 120 is not provided with an additional processor for processing the signal detected by the sensing unit 121. Accordingly, the entire configuration of the sensor device 100 mounted on the mobile robot 4 is simplified, and the mass of the sensor device 100 may be minimized. Through this, power consumption consumed by the mobile robot 4 may be minimized, and a moving distance (or operating time) of the mobile robot 4 may be increased.

The pair of doors may include a first door 131 disposed adjacent to the first vent 117 so as to selectively block the first vent 117 formed on the sensor housing 110. The pair of doors may also include a second door 132 disposed adjacent to the second vent 118 so as to selectively block the second vent 118.

The opening/closing device 140 may operate the first door 131 and the second door 132, and as a result the first vent 117 and the second vent 118 may be selectively opened. To this end, the opening/closing device 140 may include a driving unit 141 configured to generate power, and a power delivery device 150 to transfer the power generated by the driving unit 141 to the first door 131 and the second door 132.

The driving unit 141 may be an electric motor that generates power with supplied power.

Figure 7:
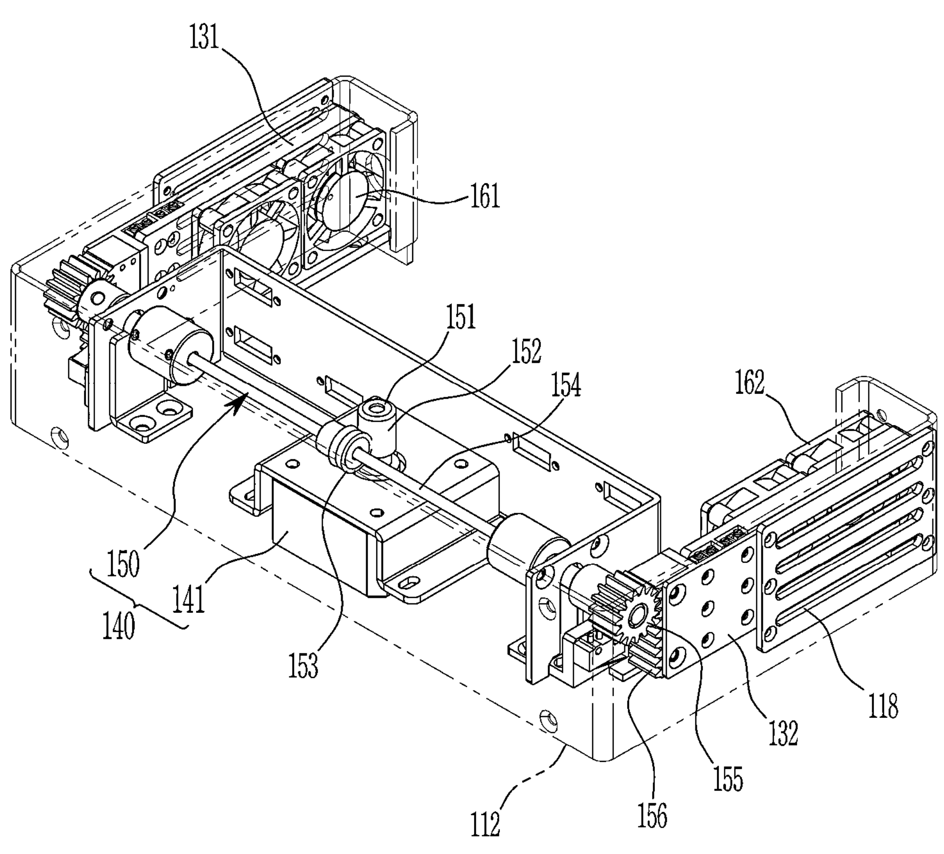
FIG. 7 is a perspective view of a sensor device according to an embodiment of the present disclosure excluding some components.

Referring to FIG. 7, the power delivery device 150 may include a worm wheel 152 provided on a drive shaft 151 of the driving unit 141, and a worm gear 153 provided on a transfer shaft 154 and engaged (e.g., gear-engaged) with the worm wheel 152. The power delivery device 150 may also include first and second intermediate gears 155 provided on both sides of the transfer shaft 154, and first and second rack gears 156 provided on the first door 131 and the second door 132, respectively. The first and second rack gears 156 are gear-engaged with the first and second intermediate gears 155, respectively.

Figure 8A:
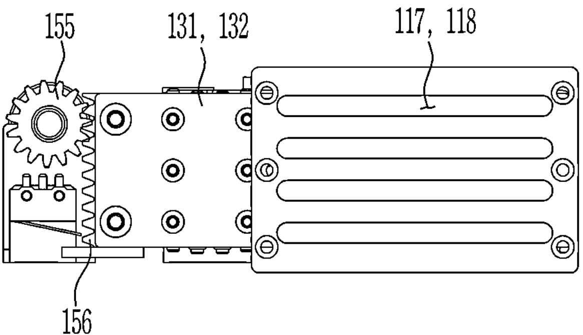
FIGS. 8A and 8B are operation diagrams for explaining an operation of a door according to an embodiment of the present disclosure.
Figure 8B:
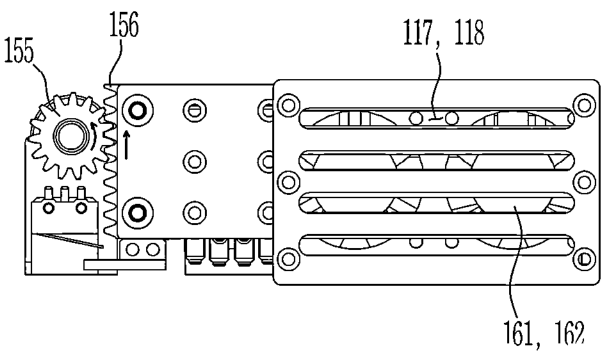

Referring to FIGS. 8A and 8B, when the worm wheel 152 rotates by a rotation of the drive shaft 151, the worm gear 153 that is gear-engaged with the worm wheel 152 rotates. When the transfer shaft 154 rotates by a rotation of the worm gear 153, a first intermediate gear 155 and a second intermediate gear 155 provided on both side end portions of the transfer shaft 154 rotate. When the first intermediate gear 155 and the second intermediate gear 155 rotate, a first rack gear 156 gear-engaged with the first intermediate gear 155 moves upward to open the first door 131, and a second rack gear 156 gear-engaged with the second intermediate gear 155 moves downward to open the second door 132.

The closing operation of the first door 131 and the second door 132 is opposite to the opening operation of the first door 131 and the second door 132 described above.

As such, since the two doors (131, 132) may be opened or closed through the single driving unit 141, the configuration of the sensor device 100 may be simplified, and manufacturing cost and weight may be reduced.

Referring back to FIGS. 3-5, the pair of fans (161, 162) configured to flow air in and out of the sensor housing 110 may include a first fan 161 disposed adjacent to the first vent 117, and a second fan 162 disposed adjacent to the second vent 118. The first fan 161 and the second fan 162 may be electric fans operated by supplying power.

The sensor device 100 according to the present disclosure may further include an air induction device 170 configured to guide air to flow over the plurality of sensor modules 120.

Figure 9:
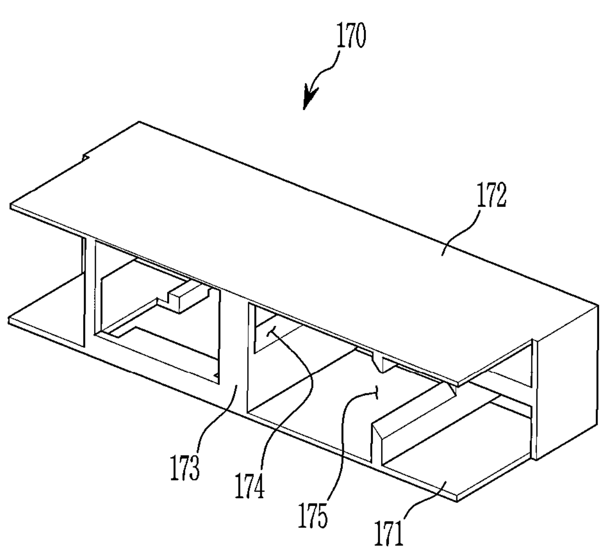
FIG. 9 is a perspective view illustrating a configuration of an air induction device according to an embodiment of the present disclosure.
Figure 10:
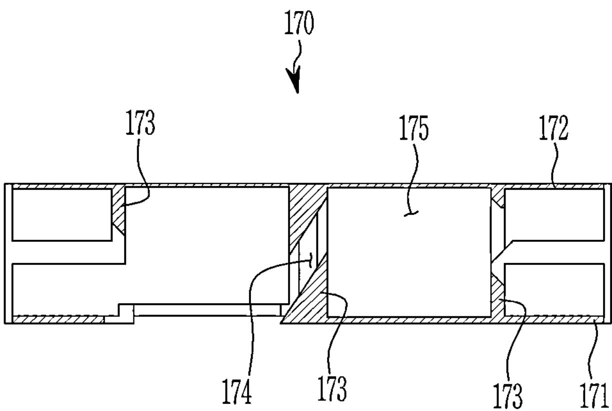
FIG. 10 is a cross-sectional view illustrating a configuration of an air induction device according to an embodiment of the present disclosure.

Referring to FIGS. 9 and 10, when the plurality of sensor modules 120 are mounted inside the sensor device 100, external air may not flow smoothly to the sensing unit 121 of the sensor module 120 due to the sensor modules 120 or other components. In order to solve this problem, the air induction device 170 is mounted inside the sensor housing 110, such that external air introduced through the first vent 117 and/or the second vent 118 may promptly flow to the sensing unit 121 of the plurality of sensor modules 120.

In order to smoothly supply external air to the plurality of sensor modules 120 mounted inside the sensor housing 110, the plurality of sensor modules 120 are sequentially disposed between the first vent 117 and the second vent 118. The sensing units 121 of the plurality of sensor modules 120 may be alternately disposed in a vertical direction. In other words, the sensing units 121 of adjacent sensor modules 120 may be disposed opposite to each other in the vertical direction.

For example, when the four sensor modules 120 are provided in the sensor device 100, the sensing unit 121 of a first sensor module 120 that is disposed closest to the first vent 117 is disposed adjacent to the first vent 117. The sensing unit 121 of a second sensor module 120 that is adjacent to the first sensor module 120 is disposed to be positioned lower than the sensing unit 121 of the first sensor module 120. The sensing unit 121 of a third sensor module 120 that is adjacent to the second sensor module 120 is disposed to be positioned lower than the sensing unit 121 of the second sensor module 120. In addition, the sensing unit 121 of the fourth sensor module 120 that is adjacent to a third sensor module 120 is disposed to be positioned lower than the sensing unit 121 of the third sensor module 120, and disposed adjacent to the second vent 118.

Each of the sensor modules 120 (the first sensor module 120 to the fourth sensor module 120) may be disposed in the air induction device 170.

The air induction device 170 may include a bottom plate 171, an upper plate 172 provided above the bottom plate 171, and at least one partition wall 173 disposed between the bottom plate 171 and the upper plate 172. A seating portion 175 on which the sensor module 120 is seated is formed by the bottom plate 171, the upper plate 172, and the partition wall 173.

In the present disclosure, three partition walls 173 are formed, each of the sensor modules 120 may be separated by the partition walls 173. In other words, the number of partition walls 173 may be one less than the number of sensor modules 120. An air induction hole 174 is formed in each partition wall 173. The air induction hole 174 is formed to fluidically connect the sensing units 121 of the sensor modules 120, minimizing the distance between them.

For example, the air induction hole 174 formed on the partition wall 173 provided between the first sensor module 120 and the second sensor module 120 is formed in a top-down direction so as to connect the sensing unit 121 of the first sensor module 120 and the sensing unit 121 of the second sensor module 120 in a minimal distance. The air induction hole 174 formed on the partition wall 173 provided between the second sensor module 120 and the third sensor module 120 is formed in a bottom-up direction so as to connect the sensing unit 121 of the second sensor module 120 and the sensing unit 121 of the third sensor module 120 in a minimal distance. In addition, the air induction hole 174 formed on the partition wall 173 provided between the third sensor module 120 and the fourth sensor module 120 is formed in a bottom-up direction so as to connect the sensing unit 121 of the third sensor module 120 and the sensing unit 121 of the fourth sensor module 120 in a minimal distance.

As such, external air introduced from the first vent 117 by the air induction device 170 may be quickly supplied to the sensing units 121 of the sensor modules 120, thus allowing any chemical substance to be detected within a short amount of time.

If desired, the sensor device 100 according to the present disclosure may further include a controller configured to control the operation of the first fan 161, the second fan 162, and the opening/closing device 140. To this end, the controller may be implemented with one or more processors that operate according to a preset program. Furthermore, program instructions programmed to perform each step of a method according to the present disclosure through the one or more processor are stored in the memory of the controller.

In some embodiments, the controller may not be provided in the sensor device 100. Instead, the operation of the first fan 161, the second fan 162, and the opening/closing device 140 may be controlled by a main controller provided in the mobile robot 4.

Hereinafter, an operation of the mobile robot 4 including the sensor device 100 according to the present disclosure is described with reference to the accompanying drawings.

Figure 11:
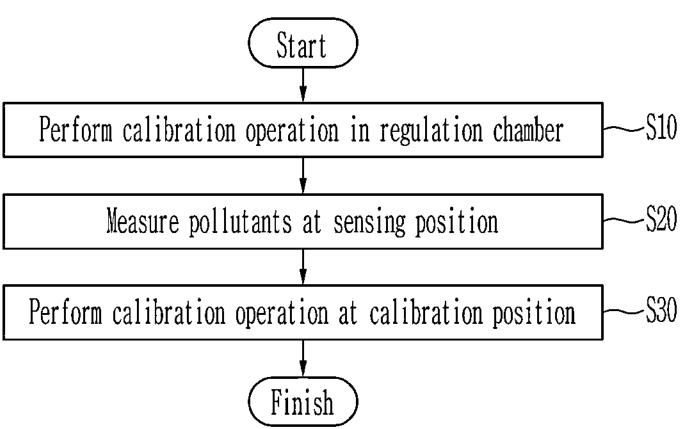
FIG. 11 is a flowchart illustrating an operation of a mobile robot according to an embodiment of the present disclosure.

FIG. 11 is a flowchart explaining an operation of the mobile robot 4 according to the present disclosure.

Referring to FIG. 11, at step S10, according to an instruction of the control server 1, the mobile robot 4 performs the calibration operation of the sensor device 100 in a regulation chamber 2.

The pressure, temperature, and humidity in the regulation chamber 2 are in a state of satisfying the standard pressure, standard temperature, and standard humidity conditions. The calibration operation (e.g., initialization operation) of the sensor device 100 is performed. As described above, the calibration operation of the sensor device 100 means a process of removing pollutants when pollutants are adsorbed by the sensing units 121 of the sensor modules 120 mounted within the sensor device 100.

When the correction operation is performed, the opening/closing device 140 is operated by the controller, and the first door 131 and the second door 132 are opened. In addition, by the controller, the first fan 161 is operated in a direction to discharge air into the mounting space 114 of the sensor housing 110, and the second fan 162 operates in a direction to discharge air from the mounting space 114 of the sensor housing 110 to the outside. Accordingly, a negative pressure is formed in the mounting space 114 of the sensor housing 110, and pollutants adsorbed to the sensing units 121 of the sensor modules 120 are quickly discharged to an outside of the sensor housing 110. When the calibration operation of the sensor module 120 is finished, the first door 131 and the second door 132 are blocked, and the mounting space 114 of the sensor housing 110 is closed and sealed.

At step S20, when the mobile robot 4 moves to the sensing position within the industry site, the sensor device 100 measures whether pollutants (e.g., noxious gas) are included in the external air.

When the mobile robot 4 detects whether the external air is polluted at the sensing position (e.g., within a factory of the industry site), the opening/closing device 140 is operated by the controller to open the first door 131 and the second door 132.

In addition, by the controller, the first fan 161 operates in a direction to introduce air into the mounting space 114 of the sensor housing 110, and the second fan 162 operates in a direction to discharge air from the mounting space 114 of the sensor housing 110 to the outside. Accordingly, the external air is introduced into the mounting space 114 of the sensor housing 110 through the first vent 117, and discharged to the outside of the sensor housing 110 through the second vent 118. In addition, when the flow rate of the external air flowing into the mounting space 114 of the sensor housing 110 is stabilized while waiting a predetermined time to lapse, the plurality of sensor modules 120 detects the chemical substance contained in the external air.

Since the external air introduced through the first vent 117 passes through the plurality of sensor modules 120 through the air induction device 170, the chemical substance included in the external air may be promptly detected. When the measurement of the external air by the sensor module 120 is finished, the first door 131 and the second door 132 are blocked, and the mounting space 114 of the sensor housing 110 is closed and sealed.

At step S30, when the mobile robot 4 moves outside the factory of the industry site after performing the sensing operation at the sensing position within the industry site, the calibration operation of the sensor device 100 is performed.

When the mobile robot 4 calibrates the sensor device 100 at the calibration position (e.g., outside the factory of the industry site), the opening/closing device 140 is operated by the controller to open the first door 131 and the second door 132.

In addition, by the controller, the first fan 161 is operated in the direction to discharge air into the mounting space 114 of the sensor housing 110, and the second fan 162 operates in a direction to discharge air from the mounting space 114 of the sensor housing 110 to the outside. Accordingly, a negative pressure is formed in the mounting space 114 of the sensor housing 110, and pollutants adsorbed by the sensing units 121 of the sensor modules 120 are quickly discharged to the outside of the sensor housing 110. When the calibration operation of the sensor module 120 is finished, the first door 131 and the second door 132 are blocked, and the mounting space 114 of the sensor housing 110 is closed and sealed.

Hereinafter, the configuration of the sensor device 100 according to another embodiment of the present disclosure is described in detail with reference to the accompanying drawings.

Figure 12:
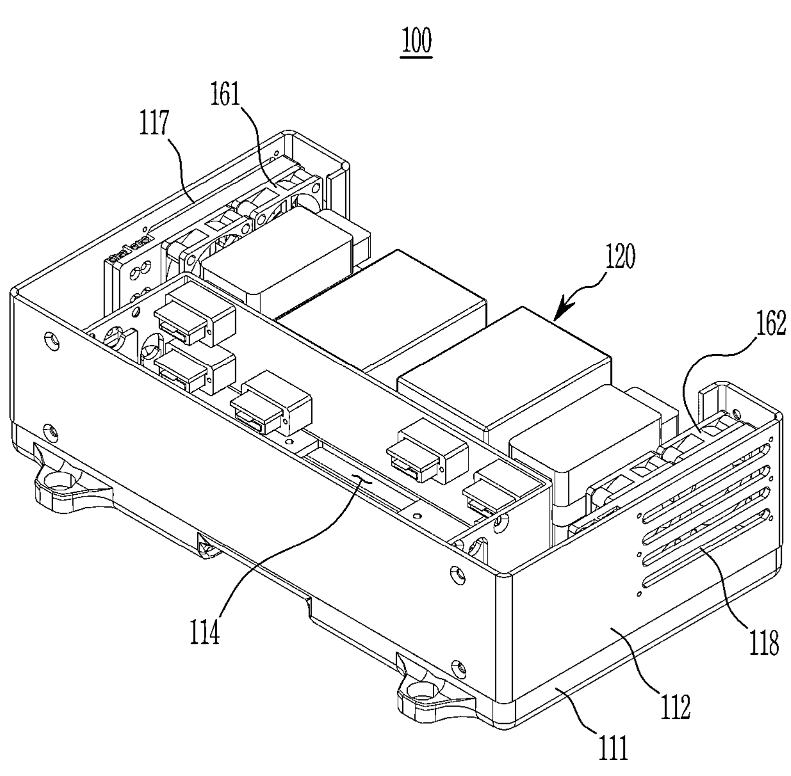
FIG. 12 is a perspective view illustrating a configuration of a sensor device according to another embodiment of the present disclosure.
Figure 13:
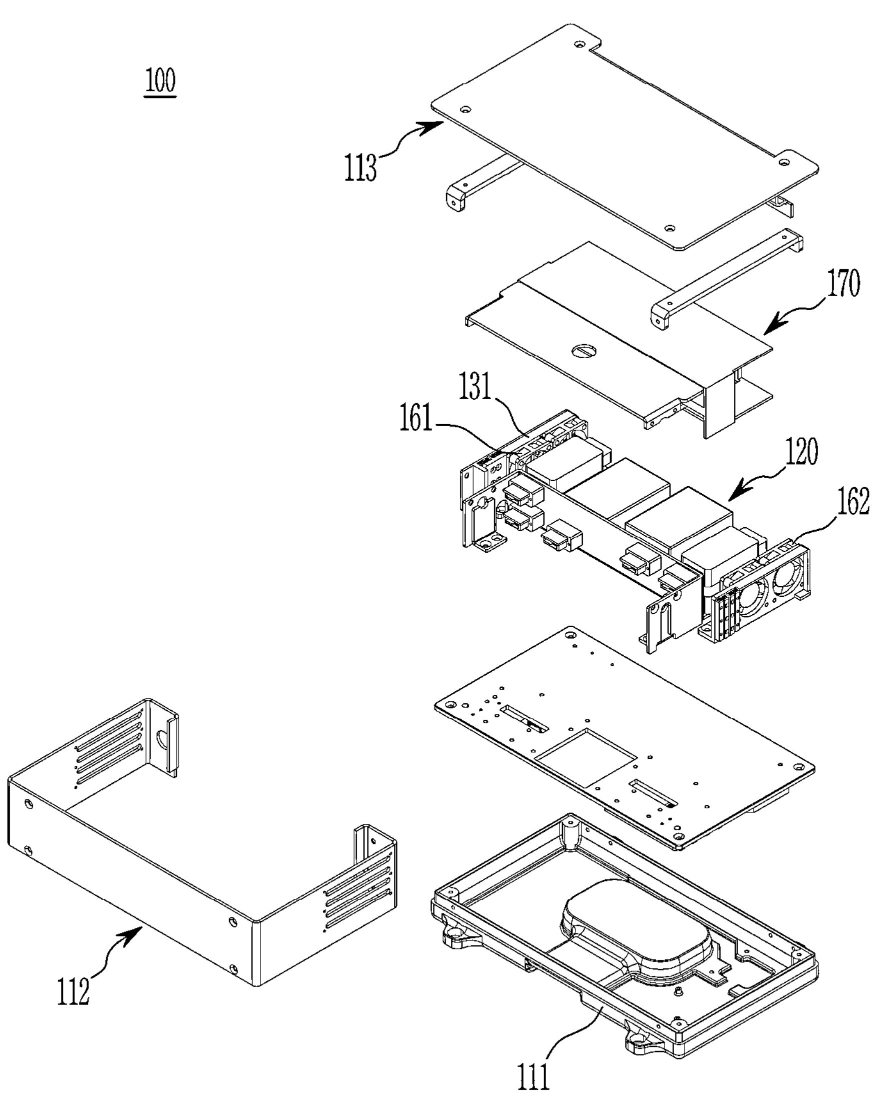
FIG. 13 is an exploded perspective view illustrating a configuration of a sensor device according to another embodiment of the present disclosure.

Referring to FIGS. 12 and 13, in the sensor device 100 according to another embodiment of the present disclosure, the doors and the power delivery device 150 are removed, compared to the above-described sensor device 100. In addition, other configurations except for the doors and the power delivery device 150 are the same as the above-described sensor device 100.

Hereinafter, an operation of the sensor device 100 according to another embodiment of the present disclosure is described in detail.

When the mobile robot 4 performs the calibration operation of the sensor device 100 in the regulation chamber 2, by the controller, the first fan 161 is operated in the direction to discharge air into the mounting space 114 of the sensor housing 110, and the second fan 162 operates in a direction to discharge air from the mounting space 114 of the sensor housing 110 to the outside. Accordingly, a negative pressure is formed in the mounting space 114 of the sensor housing 110, and pollutants adsorbed by the sensing units 121 of the sensor modules 120 are quickly discharged to the outside of the sensor housing 110.

When the mobile robot 4 moves from the regulation chamber 2 to the sensing position, by the controller, the first fan 161 and the second fan 162 operate in a direction to discharge air from the mounting space 114 to the outside. Accordingly, the external air of the sensor housing 110 is blocked from flowing into the mounting space 114.

When the mobile robot 4 has moved to the sensing position and detects whether the external air is polluted, by the controller, the first fan 161 operates in a direction to introduce air into the mounting space 114 of the sensor housing 110, and the second fan 162 operates in a direction to discharge air from the mounting space 114 of the sensor housing 110 to the outside. Accordingly, the external air is introduced into the mounting space 114 of the sensor housing 110 through the first vent 117, and discharged to the outside of the sensor housing 110 through the second vent 118. In addition, when the flow rate of the external air flowing into the mounting space 114 of the sensor housing 110 is stabilized while waiting a predetermined time to lapse, the plurality of sensor modules 120 detects the chemical substance contained in the external air. Since the external air introduced through the first vent 117 passes through the plurality of sensor modules 120 through the air induction device 170, the chemical substance included in the external air may be promptly detected. When the measurement of the external air by the sensor module 120 is finished, the first door 131 and the second door 132 are blocked, and the mounting space 114 of the sensor housing 110 is closed and sealed.

When the mobile robot 4 has moved to the calibration position and calibrates the sensor device 100, by the controller, the first fan 161 is operated in the direction to discharge air into the mounting space 114 of the sensor housing 110, and the second fan 162 operates in a direction to discharge air from the mounting space 114 of the sensor housing 110 to the outside. Accordingly, a negative pressure is formed in the mounting space 114 of the sensor housing 110, and pollutants adsorbed by the sensing units 121 of the sensor modules 120 are quickly discharged to the outside of the sensor housing 110.

According to the sensor device 100 mounted on the mobile robot 4 according to the present disclosure, since the control signal and power is supplied from the mobile robot 4, the sensor device 100 may be down-sized. Accordingly, the load applied to the mobile robot 4 may be decreased, and the operating time (e.g., moving distance) of the mobile robot 4 may be increased.

In addition, when the mobile robot 4 moves to the sensing position, the interior of the sensor housing 110 is closed and sealed, thereby sealing the sensor module 120 from being contaminated by external factors.

In addition, when the mobile robot 4 moves to the calibration position, the reliability of the sensor module 120 may be enhanced by the calibration operation of the sensing module.

While this disclosure has been described in connection with what is presently considered to be practical embodiments, it is to be understood that the disclosure is not limited to the disclosed embodiments. However, on the contrary, the disclosure is intended to cover various modifications and equivalent arrangements included within the spirit and scope of the appended claims.

DESCRIPTION OF SYMBOLS

1: control server
2: regulation chamber
3: personal portable terminal
4: the mobile robot
100: sensor device
110: sensor housing
111: lower case
112: intermediate case
113: upper case
114: mounting space
117: first vent
118: second vent
120: sensor module
121: sensing unit
122: conversion unit
123: interface unit
131: first door
132: second door
140: opening/closing device
141: driving unit
150: power delivery device
151: drive shaft
152: worm wheel
153: worm gear
154: transfer shaft
155: intermediate gear
156: rack gear
161: first fan
162: second fan
170: air induction device
171: bottom plate
172: upper plate
173: partition wall
174: air induction hole
175: seating portion

What is claimed is:

1. A sensor device, comprising:

a sensor housing forming a mounting space and including a first vent and a second vent through which air flows in and out;

a plurality of sensor modules provided in the mounting space of the sensor housing;

a first door and a second door configured to selectively block the first and second vents of the sensor housing, respectively;

an opening/closing device configured to operate the first and the second doors; and a first fan and a second fan configured to introduce air into the sensor housing, or discharge air inside the sensor housing to an outside.

2. The sensor device of claim 1, wherein a sensor module of the plurality of sensor modules comprises:

a sensing unit configured to detect a chemical substance contained in the air introduced into the sensor housing; and an interface unit configured to directly transmit a signal detected by the sensing unit to a mobile unit.

3. The sensor device of claim 1, wherein the opening/closing device comprises:

a driving unit configured to generate power; and a power delivery device configured to transfer the power generated by the driving unit to the first and second doors.

4. The sensor device of claim 3, wherein the power delivery device comprises:

a worm wheel provided on a drive shaft of the driving unit;

a worm gear provided on a transfer shaft and engaged with the worm wheel;

a pair of intermediate gears, wherein each intermediate gear is provided on a side of the transfer shaft; and a rack gear provided on each of the first and the second doors, and engaged with each intermediate gear.

5. The sensor device of claim 1, wherein:

the first and second vents are provided on both side surfaces of the sensor housing, respectively;

the first and the second doors are provided on the first and second vents, respectively; and the first and the second fan are provided on the first and second vents, respectively.

6. The sensor device of claim 5, wherein the first and second vents are disposed to face each other.

7. The sensor device of claim 1, further comprising an air induction device configured to guide air from the first and second vents to pass through the plurality of sensor modules.

8. The sensor device of claim 7, wherein the air induction device comprises:

a bottom plate;

an upper plate configured to form a seating portion on which a sensor module of the plurality of sensor modules is seated in cooperation with the bottom plate; and at least one partition wall provided between the bottom plate and the upper plate, and configured to form the seating portion on which the sensor module of the plurality of sensor modules is seated in cooperation with the bottom plate and the upper plate, wherein an air induction hole is formed in the at least one partition wall.

9. The sensor device of claim 1, wherein, at a sensing position for measuring pollutants of external air:

the first door and the second door are opened;

the first fan operates in a direction to introduce air into the mounting space; and the second fan operates in a direction to discharge air from the mounting space to the outside.

10. The sensor device of claim 1, wherein, at a calibration position to calibrate a sensor module of the plurality of sensor modules:

the first door and the second door are opened; and the first fan and the second fan operate in a direction to discharge air from the mounting space to the outside so as to form negative pressure in the mounting space.

11. A sensor device, comprising:

a sensor housing forming a mounting space and including a first vent and a second vent through which air flows in and out;

a plurality of sensor modules provided in the mounting space of the sensor housing;

a first fan provided on the first vent;

a second fan provided on the second vent; and an air induction device configured to guide air from the first and second vents to pass through the plurality of sensor modules, wherein the air induction device comprises:

a bottom plate;

an upper plate configured to form a seating portion on which a sensor module of the plurality of sensor modules is seated in cooperation with the bottom plate; and at least one partition wall provided between the bottom plate and the upper plate, and configured to form the seating portion on which the sensor module of the plurality of sensor modules is seated in cooperation with the bottom plate and the upper plate, and wherein an air induction hole is formed in the at least one partition wall.

12. The sensor device of claim 11, wherein the first and second vents are provided to face each other.

13. The sensor device of claim 11, wherein, at a sensing position to measure pollutants of external air:

the first fan operates in a direction to introduce air into the mounting space; and the second fan operates in a direction to discharge air from the mounting space.

14. The sensor device of claim 11, wherein, at a calibration position to calibrate a sensor module of the plurality of sensor modules:

the first fan and the second fan operate in a direction to discharge air from the mounting space to an outside so as to form negative pressure in the mounting space.

* * * * *